US010959871B2

(12) United States Patent
Turrini et al.

(10) Patent No.: US 10,959,871 B2
(45) Date of Patent: Mar. 30, 2021

(54) ORTHOSIS WITH CONTROLLED ANGULAR EXCURSION

(71) Applicant: F.G.P. S.r.l., Villafranca di Verona (IT)

(72) Inventors: Alberto Turrini, Villafranca di Verona (IT); Moreno Ferrigolo, Villafranca di Verona (IT)

(73) Assignee: F.G.P. S.r.l., Villafranca di Verona (IT)

( * ) Notice: Subject to any disclaimer, the term of this patent is extended or adjusted under 35 U.S.C. 154(b) by 290 days.

(21) Appl. No.: 15/763,770

(22) PCT Filed: Sep. 9, 2016

(86) PCT No.: PCT/EP2016/071377
§ 371 (c)(1),
(2) Date: Mar. 27, 2018

(87) PCT Pub. No.: WO2017/071863
PCT Pub. Date: May 4, 2017

(65) Prior Publication Data
US 2018/0271689 A1     Sep. 27, 2018

(30) Foreign Application Priority Data

Oct. 30, 2015   (IT) .............................. UB2015A5355

(51) Int. Cl.
*A61F 5/01*        (2006.01)
(52) U.S. Cl.
CPC .... *A61F 5/0125* (2013.01); *A61F 2005/0139* (2013.01); *A61F 2005/0172* (2013.01)

(58) Field of Classification Search
CPC ...... A61F 2005/0172; A61F 2005/0146; A61F 2005/0132; A61F 2005/0137;
(Continued)

(56) References Cited

U.S. PATENT DOCUMENTS 4,632,098 A * 12/1986 Grundei ................ A61F 5/0106
602/26
6,436,066 B1 * 8/2002 Lockhart ............... A61F 5/0125
602/26

(Continued)

OTHER PUBLICATIONS

International Search Report for PCT Application No. PCT/EP2016/071377 dated Nov. 3, 2016 in 4 pages.
(Continued)

*Primary Examiner* — Alireza Nia
*Assistant Examiner* — Kevin S Albers
(74) *Attorney, Agent, or Firm* — Knobbe, Martens, Olson & Bear, LLP

(57) ABSTRACT

An orthosis with controlled angular excursion can be positioned at the level of a joint or articulation of the human body. The orthosis includes an articulated joint with a basic structure designed to be positioned on the joint and also includes centrally, a pin with toothing located in a circular sector with predetermined width. The basic structure and the relative pin provided with toothing are equipped with a respective pair of rings, each of which has a substantially elongated shape. A hollow part, or slot, includes two straight sectors, of which at least one is provided with toothing with the same pitch as the toothing of the pin with which it engages. The pair of rings can, when in use, be simultaneously rotated around the pin, and are provided with slots which in turn include a tractor for the orthosis.

6 Claims, 3 Drawing Sheets

(58) Field of Classification Search
CPC .. A61F 2005/0139; A61F 5/0125; A61F 5/00;
A61F 5/0123; A61F 5/01; A61F 5/0102;
A61F 5/0127; A61F 5/013; A61F 5/042;
A61F 5/048; A61F 2005/0148; A61F
2005/0151; A61F 2005/0153; A61F
2005/0158; A61F 2005/016; A61F
2005/0162; Y10T 16/541; Y10T 16/5445;
Y10T 16/5361; Y10T 16/52; Y10T
16/546; Y10T 403/32861; A44B 11/2588;
F04C 2270/0421; A63H 3/46; E05D
3/122; E05Y 2201/62; A61H 1/024;
A61H 1/0274
USPC .......................................... 602/16; 403/52, 61
See application file for complete search history.

(56) References Cited

U.S. PATENT DOCUMENTS

| | | | |
|---|---|---|---|
| 6,551,264 B1 | 4/2003 | Cawley et al. | |
| 8,167,829 B2* | 5/2012 | Sterling | A61F 5/0123 602/16 |
| 2002/0133108 A1 | 9/2002 | Jagodzinski | |
| 2003/0100853 A1* | 5/2003 | Yamasaki | A61F 5/0123 602/16 |
| 2004/0165939 A1* | 8/2004 | Marche | F16C 11/04 403/52 |
| 2005/0187506 A1* | 8/2005 | Reinhardt | A61F 5/0125 602/30 |
| 2007/0244419 A1* | 10/2007 | Mason | A61F 5/0123 602/16 |
| 2013/0172797 A1 | 7/2013 | Merkley et al. | |
| 2014/0336553 A1* | 11/2014 | De Cortanze | A61F 5/0125 602/16 |
| 2018/0209618 A1* | 7/2018 | Pontano | F21V 21/0816 |

OTHER PUBLICATIONS

Written Opinion for PCT Application No. PCT/EP2016/071377 dated Nov. 3, 2016 in 5 pages.

* cited by examiner

ORTHOSIS WITH CONTROLLED ANGULAR EXCURSION

CROSS-REFERENCE TO RELATED APPLICATIONS

This application is the U.S. National Phase under 35. U.S.C. § 371 of International Application PCT/EP2016/071377, filed Sep. 9, 2016, which claims priority to Italian Patent Application UB2015A005355 filed on Oct. 30, 2015.

TECHNICAL FIELD

The present invention relates to an orthosis with controlled angular excursion, fitted with a tensioner eccentric articulated joint. More specifically, this invention relates to an orthopedic orthosis or brace designed for the rehabilitation of the joints of the human body such as the knee, the elbow, the ankle, the shoulder and similar.

The orthosis according to this invention comprises an articulated joint that can allow one, two or more parts to rotate with respect to a fixed part, with a variable distance with respect to the centre of rotation, in proportion to the rotation performed.

According to the invention in fact, the rotated parts not only vary their angular position with respect to the main axis of the fixed part but can also vary their relative distance with respect to the centre of rotation located in a specific point of the fixed part.

It thus ensues that the rotated parts (whether driven or driving) vary the total length of the entire system, according to the angle measured between the rotated parts.

This invention can be applied in the medical and orthopedic industry and in particular in the production of braces in general, as well as of prostheses and orthoses mainly used in conservative, post-traumatic, re-educational and post-operative therapy.

BACKGROUND ART

The use is known in the orthopedic sector of orthopedic braces or orthoses by subjects presenting orthopedic problems involving the knee joint, but similarly also of other joints, such as the ankle or the elbow, above all in the case of injuries or as a result of a previous surgical operation.

In general, the orthopedic brace or orthosis is designed to guarantee or control the hinge restraint function of joints, for example between the femur and the tibia in the case of the knee, but also of other articulated joint points, for example the elbow, supporting stress which would otherwise be harmful for the joint.

The function of an orthosis is, in general, that of guaranteeing the relative immobilization or limitation of a joint affected by trauma, by arthrosis, by sprained ligaments or which has undergone a surgical operation.

Another use of orthoses is for the concomitant functional rehabilitation or re-education, wherein the orthosis can be used to reduce the load on the joint and reduce the pain, or can be used for prevention in cases of osteoporosis or bone weakness.

An orthosis usually comprises a rigid or soft frame, encircling the limb, designed to guarantee adequate harnessing of the joint in order to prevent the onset of stress on the ligaments or on the synovial membranes during walking by the injured and/or convalescent subject.

According to background art, the frame of an orthosis for joints, for example in the typical case of a knee brace, comprises means of restraint to the femur and the tibia and a section of connection of these means consisting of an articulated joint positioned at the level of the knee.

The means of restraint usually consist of preformed bars that are fixed by means of suitable straps encircling both the femur and the tibia of the injured subject or fabric bands, straps or sleeves that make it possible to create a restraint between the ends of the mechanical articulated joint and the limb.

The mechanical articulated joint is positioned laterally with respect to the femur and the tibia, in the case of application, for example, to the leg. Thanks to its conformation consisting of two rotation centres relatively restrained to each other by toothed profiles, this articulated joint follows the kinematics of the knee with good approximation.

A standard multicentre articulated joint is a system consisting of two hinged bars, each one hinged to its own centre of rotation, wherein these centres of rotation are restrained parallel to each other and at a known distance.

In the standard multicentre articulated joint, the two bars are connected to each other thanks to a circular toothed profile present on each bar, and this toothed profile places them in relative and synchronous motion with respect to each other.

In this articulated joint, by definition, the rotation centres and the toothed profile enable the bars to rotate only around two parallel axes and their rotation motion thus lies on one plane.

Various solutions and types of joints are used to correct several problems, for example through the use of special knee braces aimed at correcting the misalignment of the joint, generally through the use of shims of various types inserted inside the brace close to the lateral thrust area to be fitted on the articulated joint.

While clinically and at least partially resolving limb deformities, the solutions proposed above are not without drawbacks substantially connected with the use of the orthosis.

One problem is that the articulations of the human body, such as the knee, especially in the case of disease or other problems during walking, move in an irregular way, that is to say not exactly on a rotation plane. This means that traditional orthoses are not suitable for angular movements, since the rotated parts only change their angular position with respect to the main axes of the fixed part, since it is impossible due to their construction conception for them also to change their relative distance with respect to the centre of rotation located in a specific position of the fixed part, thus also making it impossible to vary the total length of the entire system in following the anatomical movements of the limb.

This means that since they are not designed to follow the anatomical variations in length that occur during the angular movement of a joint, standard type braces lose adherence during movement of the limb, making it impossible for the brace to follow the limb, thereby losing the function for which it was designed.

Another problem is that, taking the knee joint into consideration, it was noted that during movement, when walking for example, the tension varies according to the position of the knee, which will tend to be overloaded in the angles between 30° and 0° in extension, that is to say in a sector wherein the weight of the body weighs more heavily on the joint precisely when it needs greater stability.

Document U.S. Pat. No. 6,551,264 B1 discloses an orthosis that is mountable on a knee having a femoral head and patella. The orthosis has upper and lower arms positionable about the knee and a hinge assembly positioned between the upper and lower arms at the knee to one side of the patella. A compression member is positioned at the femoral head adjacent to the patella on the opposite side of the patella from the hinge assembly.

DESCRIPTION OF THE INVENTION

This invention proposes to provide an orthosis with controlled angular excursion fitted with a tensioner eccentric articulated joint that is able to eliminate or at least reduce the drawbacks described above.

The invention also proposes to provide an orthosis comprising a tensioner eccentric articulated joint that is designed to allow one, two or several parts to rotate with respect to a fixed part, with a variable distance with respect to the centre of rotation, in proportion to the rotation performed.

This is achieved by means of an orthosis with controlled angular excursion whose features are described in the main claim.

The dependent claims of the solution according to this invention describe advantageous forms of embodiment of the invention.

The main advantages of this solution concern first of all the fact that the rotated parts of the joint vary not only their angular position with respect to the main axis of the fixed part but also vary their relative distance with respect to the centre of rotation located in a specific point of the fixed part.

As a result, the rotated parts, whether driven or driving, cause a variation in the total length of the entire system, depending on the angle measured between the rotated parts, for example to make the parts of an articulated orthopedic brace more integral with the part of the body on which it is fitted, following the movement more appropriately of, for example, a joint which due to its nature tends to vary in length during its movement.

DESCRIPTION OF THE DRAWINGS

Other features and advantages of the invention will become clear on reading the description given below of one embodiment, provided as a non-limiting example, with the help of the accompanying drawings, in which.

DESCRIPTION OF AN EMBODIMENT OF THE INVENTION

Figure 3:
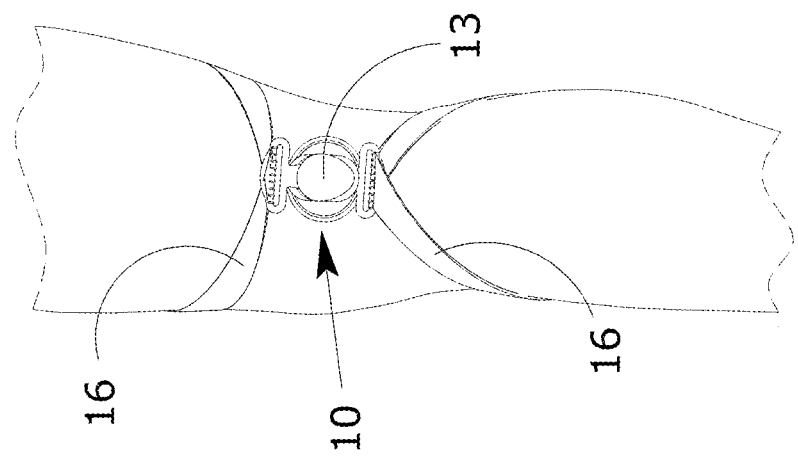
FIGS. 1 to 3 show schematic views of, respectively, the first side, the front and the second side of a knee brace fitted with a tensioner eccentric articulated joint according to the invention.
Figure 2:
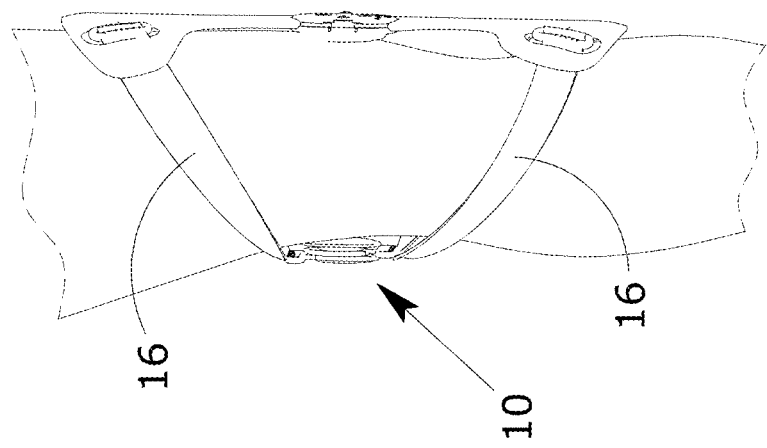
Figure 1:
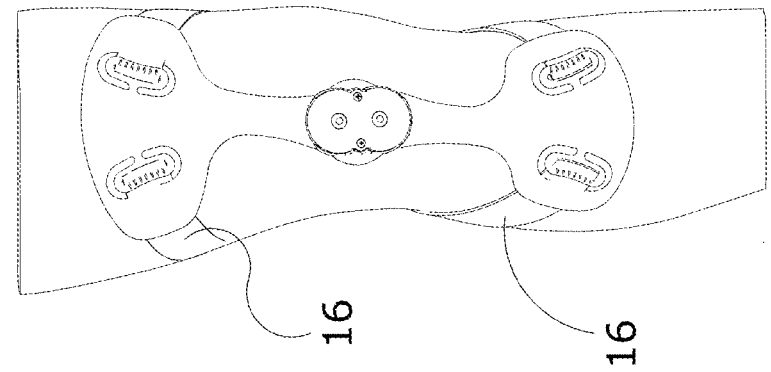
Figure 4:
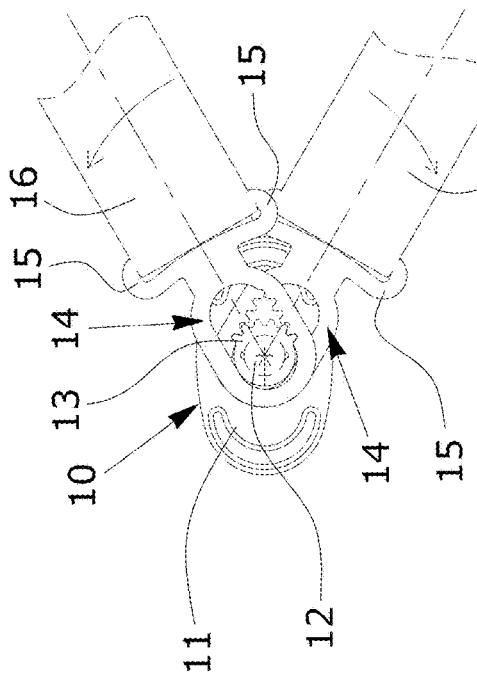
FIG. 4 shows a detailed schematic view of the central part of the joint according to the invention.
Figure 5:
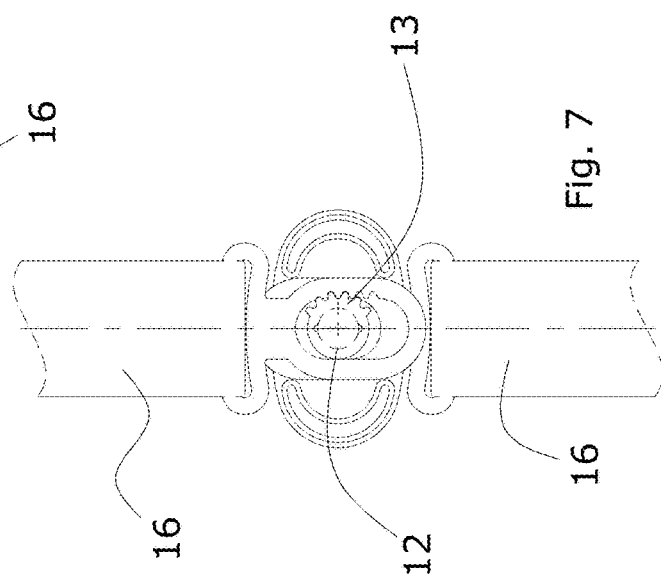
FIGS. 5 to 7 are schematic views showing three different positions that the joint according to this invention can assume.
Figure 6:
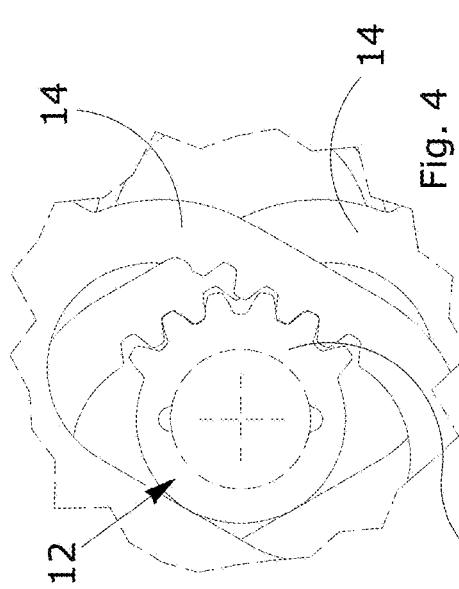
Figure 7:
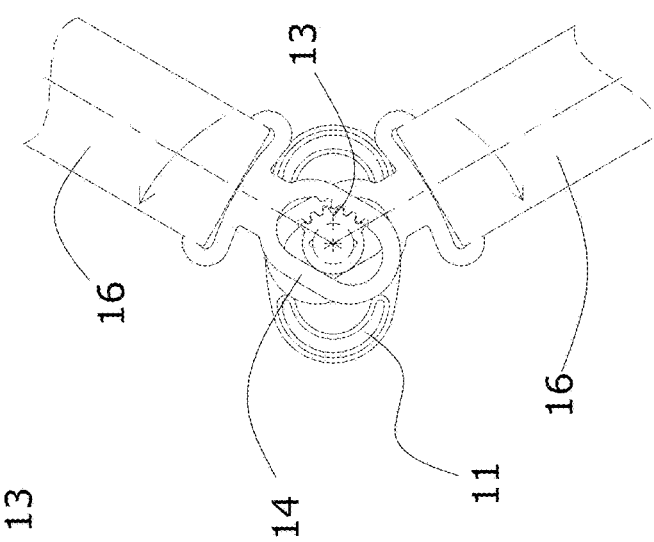

Referring initially to FIGS. 4 to 7, and in particular to FIG. 5, the numeral 10 denotes in its entirety a tensioner eccentric articulated joint for human joints or articulations, forming part of an orthosis with controlled angular excursion according to the invention.

The articulated joint 10 comprises a basic structure 11, with a substantially rounded or elliptical shape or another more appropriate shape also depending on the part of the body it is to be fitted to and the type of joint to be treated and on which it is designed to rest, such as the knee for example, which is why the inner side facing the joint is fitted with a cushioning pad which is not shown because it is a known item.

This basic structure 11 comprises, centrally, a fixed pin 12 which presents toothing 13 integral with the base which covers a circular sector of around 90°.

The basic structure 11 and the relative pin 12 provided with toothing 13 are suitable to accommodate two rings 14 with a substantially elongated shape whose hollow part, or slot, comprises two straight sectors, at least one of which is provided with toothing having the same pitch as the toothing 13 of the pin 12 with which it engages.

When in operation, the two rings 14 are parallel to the plane of the basic structure and symmetrical to a plane on which the vertical axis of the pin 12 lies, and with respect to this plane they can be moved angularly and in a reciprocally specular direction.

The rings 14, which rotate around the pin 12, as will be described below, are also provided with non-slip toothed slots 15 for the passage of straps 16 which form part of the tensioning structure of the orthosis on which the joint is fitted.

The angular movement of the rings 14 with respect to the pin 12 of the basic structure 11 determines their simultaneous translation which moves the slots 15 and the relative straps 16 away from or closer to the pin 12, since the inner toothing of the rings 14 engages specularly with the toothing 13 of the pin 12.

The movement of the slots 15 away from or closer to the pin 12 respectively determines the release or tautening of the straps 16 which are restrained on the opposite sector of the joint.

Figure 10:
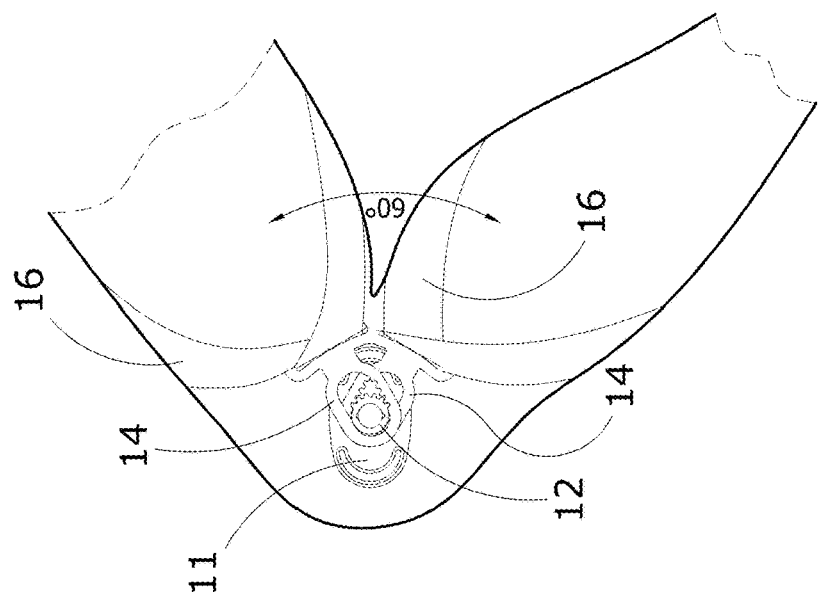
FIG. 10 is a view of the joint fitted to an orthosis worn on a leg at the level of the knee at an angle of 60°, that is to say in accentuated flexion.
Figure 9:
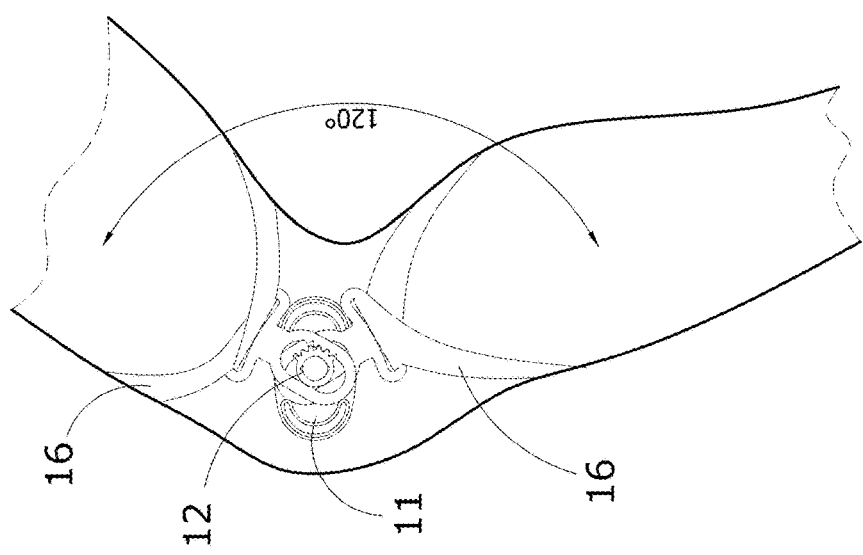
FIG. 9 is a view of the joint fitted to an orthosis worn on a leg at the level of the knee at an angle of 120°, that is to say in semi-flexion.
Figure 8:
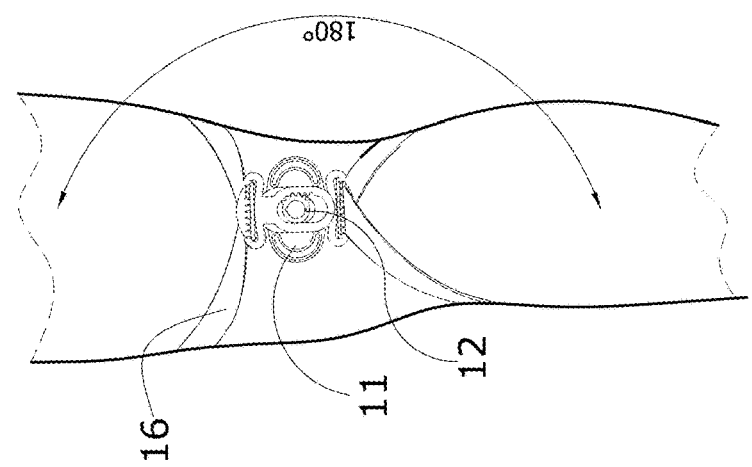
FIG. 8 is a view of the joint fitted to an orthosis worn on a leg at the level of the knee and in a first position with the leg extended, that is to say with 180° between the femur and the tibia.

This allows at least three positions of the joint according to the invention which are the most significant and which are shown in FIGS. 8, 9 and 10, considering that when the angle between the rotated parts changes, there is a proportional variation in the distance between the fixing points of the straps and the centre of rotation consisting of the vertical axis of the pin 12.

The first position shown in FIG. 8 refers to a condition of the joint wherein the rings 14 are reciprocally positioned at 180° and the distance between the centre of rotation and the slots 15 for the passage of the straps is at a minimum.

In this condition, the end of travel having been reached, the fixing points of the straps 16 are at their closest to the centre of rotation, and in this case the straps 16 are at the maximum traction permitted by the system.

If, instead of using the straps 16, two orthosis parts are used, then these would be at the least distance from the centre of rotation, thus in traction.

The second position, shown in FIG. 9, is intermediate, with an angle between the two parts of the limb, in the case shown femur and tibia, starting to decrease to around 120°. As the angle changes between the two rotating parts consisting of the rings 14, there is a proportional variation between the fixing points of the straps 16 and the centre of rotation.

In this case, the straps 16 start to be released with respect to their previous position, and if two orthosis parts are used instead of straps they would be further away from the centre of rotation as the flexing angle of the joint decreases.

The third position shown in FIG. 10 is the most closed position of the joint according to this invention, that is to say with a flexion angle around 60°, and in this case the distance between the centre of rotation and the slots 15 for the passage of the straps 16 is at a maximum and the straps are therefore slacker.

If two orthosis parts are used instead of straps, they would be furthest away from the centre of rotation, thus in the flexion and release condition, with the maximum slackening of the straps.

Intermediate flexion conditions naturally determine intermediate traction or release conditions of the straps.

The invention as described above refers to a preferred form of embodiment. It is nevertheless clear that the invention is susceptible to numerous variations falling within the scope of the disclosure, in the context of technical equivalents, for example the use of toothed edges on the opposite side of the ring 14 to the one previously described, obtaining exactly opposite results.

Although the invention is described above fitted to a knee brace, it is clear that the eccentric articulated joint according to the invention can be easily adapted to any other type of orthosis for joints, in particular for the elbow, the ankle or the shoulder.

What is claimed is:

1. An orthosis with controlled angular excursion that can be positioned adjacent to a joint or articulation of a wearer comprising:
    an articulated joint with a basic structure designed to be positioned on a joint or articulation of a wearer and which comprises, centrally, a fixed pin comprising a toothing located in a circular sector;
    wherein the basic structure and the fixed pin accommodate two rings, each of the rings has an elongated shape;
    wherein each ring has a hollow part, or slot, which comprises two straight sectors, at least one of the straight sectors is provided with toothing having the same pitch as the toothing of the fixed pin, the toothing of each straight sector being engaged with the toothing of the fixed pin;
    wherein each ring comprises a slot for the passage of a traction strap for said orthosis; and
    wherein the two rings are configured to be simultaneously rotated around the fixed pin.

2. The orthosis of claim 1, wherein the rings are rotatable relative to said fixed pin comprising a toothing, and wherein the change in the angle between the two rotating rings, with respect to the fixed pin, determines a proportional movement of the rings with respect to the fixed pin, causing the rings to move away from or closer to the center of the fixed pin, depending on whether the angle becomes more acute or more obtuse.

3. The orthosis of claim 2, in which the moving away or closer, determined by an angular movement of the rings and of the slots with respect to the fixed pin, causes respectively the release or the tensioning of the traction strap of the orthosis.

4. The orthosis of claim 1, wherein in operation the two rings are on a same plane as the vertical plane of the basic structure and arranged symmetrically with respect to a plane on which the vertical axis of the fixed pin lies, with respect to which they can be moved angularly and in a reciprocally specular direction.

5. The orthosis of claim 1, wherein the basic structure has a substantially rounded or elliptical shape and comprises a cushioning pad positioned on a side facing an inner side of a wearer's joint.

6. The orthosis of claim 3, wherein the angular movement of the rings with respect to the fixed pin of the basic structure determines their simultaneous movement, which moves the slots and the traction straps away from or closer to the fixed pin.

* * * * *